(12) United States Patent
Douglas

(10) Patent No.: US 8,330,121 B2
(45) Date of Patent: Dec. 11, 2012

(54) DYNAMIC DISPLAY AND CONTROL OF UV SOURCE FOR SANITIZATION IN MOBILE DEVICES

(75) Inventor: Ryan J. Douglas, Stillwater, MN (US)

(73) Assignee: Verilux, Inc., Waitsfield, VT (US)

( * ) Notice: Subject to any disclaimer, the term of this patent is extended or adjusted under 35 U.S.C. 154(b) by 43 days.

(21) Appl. No.: 13/099,949

(22) Filed: May 3, 2011

(65) Prior Publication Data

US 2012/0280147 A1  Nov. 8, 2012

(51) Int. Cl.
*A61L 2/10* (2006.01)
*A47L 5/00* (2006.01)

(52) U.S. Cl. ............ 250/455.11; 250/504 R; 250/493.1; 422/24; 422/186; 96/224

(58) Field of Classification Search ............ 250/455.11, 250/504 R, 493.1; 422/24, 186; 96/224
See application file for complete search history.

(56) References Cited

U.S. PATENT DOCUMENTS

| | | |
|---|---|---|
| 2,632,912 A | 3/1953 | Cuddeback |
| 3,970,856 A | 7/1976 | Machaffey et al. |
| 3,975,790 A | 8/1976 | Patterson |
| 4,686,986 A | 8/1987 | Fenyo et al. |
| 4,907,316 A | 3/1990 | Kurz |
| 4,952,369 A | 8/1990 | Belilos |
| 5,233,283 A | 8/1993 | Kennedy |
| 5,233,723 A | 8/1993 | Hung |
| 5,259,380 A | 11/1993 | Mendes et al. |
| 5,420,768 A | 5/1995 | Kennedy |
| 5,500,009 A | 3/1996 | Mendes et al. |
| 5,634,711 A | 6/1997 | Kennedy et al. |
| 5,728,090 A | 3/1998 | Martin et al. |
| 5,783,909 A | 7/1998 | Hochstein |
| 5,920,075 A | 7/1999 | Whitehead |
| 5,968,455 A * | 10/1999 | Brickley ................. 422/121 |
| 6,063,108 A | 5/2000 | Salansky et al. |
| 6,094,767 A | 8/2000 | Iimura |
| 6,239,442 B1 | 5/2001 | Iimura |
| 6,242,753 B1 | 6/2001 | Sakuri |
| 6,283,956 B1 | 9/2001 | McDaniel |
| 6,443,978 B1 | 9/2002 | Zharov |
| 6,656,424 B1 | 12/2003 | Deal |
| 6,911,177 B2 | 6/2005 | Deal |
| 6,953,940 B2 | 10/2005 | Leighley et al. |
| 6,968,595 B2 | 11/2005 | Oh et al. |
| 6,976,984 B2 | 12/2005 | Cense et al. |
| 7,173,254 B2 | 2/2007 | Sauska et al. |
| 7,175,806 B2 | 2/2007 | Deal et al. |
| 7,201,765 B2 | 4/2007 | McDaniel |
| 7,210,194 B2 | 5/2007 | Kiern |
| 7,211,813 B2 | 5/2007 | Jensen |

(Continued)

FOREIGN PATENT DOCUMENTS

WO  2005011755  2/2005

(Continued)

*Primary Examiner* — Nikita Wells
(74) *Attorney, Agent, or Firm* — Dardi & Herbert, PLLC; Curtis B. Herbert

(57) ABSTRACT

A mobile sanitizer movable across a surface to sanitize the surface. The sanitizer may comprise an ultraviolet light source that illuminates the surface and a microprocessor control. The control may adjust the light source intensity in response to a speed of the movement of the light source relative to the surface. And, for instance, the control may drive a display indicating how movement of the device relates to sanitization settings input by a user.

28 Claims, 5 Drawing Sheets

U.S. PATENT DOCUMENTS

| | | |
|---|---|---|
| RE40,403 E | 6/2008 | Cho |
| 7,444,711 B2 | 11/2008 | Garcia et al. |
| 7,476,885 B2 | 1/2009 | Garcia et al. |
| 7,507,980 B2 | 3/2009 | Garcia et al. |
| 7,581,283 B2 | 9/2009 | Yoo et al. |
| 7,610,652 B2 | 11/2009 | Seo et al. |
| 8,105,532 B2 * | 1/2012 | Harmon et al. ................. 422/24 |
| 2004/0244138 A1 | 12/2004 | Taylor et al. |
| 2005/0000543 A1 | 1/2005 | Taylor et al. |
| 2005/0022844 A1 | 2/2005 | Field et al. |
| 2005/0055070 A1 | 3/2005 | Jones et al. |
| 2005/0065579 A1 | 3/2005 | Chen et al. |
| 2005/0091785 A1 | 5/2005 | Yuen |
| 2005/0149150 A1 | 7/2005 | McDaniel |
| 2005/0228463 A1 | 10/2005 | Mac |
| 2005/0234383 A1 | 10/2005 | Dougal |
| 2005/0261750 A1 | 11/2005 | McDaniel |
| 2006/0185116 A1 | 8/2006 | Lee et al. |
| 2006/0185117 A1 | 8/2006 | Seo et al. |
| 2006/0236496 A1 | 10/2006 | Oh et al. |
| 2006/0278088 A1 * | 12/2006 | Helsel .............................. 96/224 |
| 2006/0293727 A1 | 12/2006 | Spooner et al. |
| 2007/0023710 A1 | 2/2007 | Tom et al. |
| 2007/0032843 A1 | 2/2007 | Hsu |
| 2007/0067943 A1 * | 3/2007 | Makarov ......................... 15/339 |
| 2007/0129778 A1 | 6/2007 | Dougal |
| 2007/0167999 A1 | 7/2007 | Breden et al. |
| 2007/0185553 A1 | 8/2007 | Kennedy |
| 2007/0192986 A1 | 8/2007 | Garcia et al. |
| 2007/0209143 A1 | 9/2007 | Choi et al. |
| 2007/0209144 A1 | 9/2007 | Fester et al. |
| 2007/0231193 A1 | 10/2007 | Jung et al. |
| 2008/0004611 A1 | 1/2008 | Houboult et al. |
| 2008/0052872 A1 | 3/2008 | Cho |
| 2008/0103563 A1 | 5/2008 | Powell et al. |
| 2008/0140164 A1 | 6/2008 | Oberreiter et al. |
| 2008/0256741 A1 | 10/2008 | Garcia et al. |
| 2008/0260601 A1 | 10/2008 | Lyon |
| 2008/0294227 A1 | 11/2008 | Perez |
| 2009/0114854 A1 | 5/2009 | Garcia et al. |
| 2009/0126145 A1 | 5/2009 | D'Agostino et al. |
| 2009/0183335 A1 | 7/2009 | Griffith et al. |
| 2009/0184268 A1 | 7/2009 | Garcia et al. |
| 2009/0205664 A1 | 8/2009 | Lyon |
| 2009/0240310 A1 | 9/2009 | Kennedy |

FOREIGN PATENT DOCUMENTS

| | | |
|---|---|---|
| WO | 2006015390 | 2/2006 |
| WO | 2007124569 | 11/2007 |

* cited by examiner

US 8,330,121 B2

DYNAMIC DISPLAY AND CONTROL OF UV SOURCE FOR SANITIZATION IN MOBILE DEVICES

TECHNICAL FIELD

The technical field is directed to devices with an ultraviolet light source for sanitization of surfaces, including mobile devices such as vacuum cleaners, or sanitizing wands.

BACKGROUND

Sanitization of a surface with light relates to administering doses of light of a certain wavelength or spectrum of wavelengths. The light has an intensity, with the product of intensity and time resulting in a dose. A measure of intensity is Watts/cm$^2$. The dose is typically applied per unit area; a measure of dosage is J/cm$^2$, i.e., the product of Watts/cm$^2$ and time, or Watt-seconds per cm$^2$. The light source has an intensity at the source, typically the surface of the bulb. The intensity of the source at the surface depends on the distance of the light source from the surface and how the light is focused.

Sanitization is a term that refers to making a substantial reduction of bacteria and/or viruses at a surface. A light that provides suitable spectra for killing bacteria or viruses is generally referred to as a germicidal light source.

SUMMARY

Effective sanitization with an ultraviolet light source requires a light source with substantial intensity. Maintaining a high intensity is desirable for achieving an effective kill rate. It has been determined, however, that some surfaces might experience accelerated wear upon exposure to a high intensity source. Further, experiments with a variety of surfaces have indicated that a target dose of light on the surface varies considerably depending on the surface and the organism or condition that the user desires to eliminate. The dose is the product of the intensity of the light source at the surface and the time of exposure to the source.

An embodiment of the invention is a mobile sanitizer movable across a surface to sanitize the surface comprising an ultraviolet light source that illuminates the surface and a microprocessor control operably controlling the light source intensity to adjust the intensity of the light source as the light source is moved and in response to a speed of the movement of the light source relative to the surface. The controller may provide for the intensity to increase or decrease.

Another embodiment of the invention is a mobile sanitizer movable across a surface to sanitize the surface comprising an ultraviolet light source that illuminates the surface and a microprocessor control operably controlling a display that indicates to a user when a sanitization process is being successfully executed. The device may accept one or more user-inputs that contribute to selection of a goal for light dosage onto the surface. The inputs may account for one or more of a variety of factors, e.g., surface type, desired condition or organism to eliminate, and desired number of passes over an area.

DETAILED DESCRIPTION

A person using a germicidal light device to sanitize a surface can not visually detect the cumulative amount of light that has fallen upon the surface. An adequate dosage is required, however, if the surface is to be effectively sanitized, or sanitized to a predetermined standard. If the user is moving the source, tracking the total time of exposure can be difficult. At the same time, some surfaces can be damaged if the source intensity is too great at the surface.

In the case of a vacuum cleaner equipped with a germicidal light source, for instance, the rate of movement of the vacuum cleaner can vary between users and can be inconsistent for a particular user. Variations in the surface can also have significant effects; carpet, for instance, typically requires a higher dose than a smooth, hard surface to achieve the same germicidal kill rate. An intensity that is too low for a first user may be too high for a second user on the same surface. Or an intensity that is too high for a user on a first surface may be too low for the same user on a second surface.

Embodiments of the invention are described herein that provide useful, real-time feedback to a user so that a mobile sanitization device can be used effectively to achieve true sterilization or a degree of sanitization that chosen the user. This feedback integrates the user's choices while accounting for the actual operation of the device. The user can respond to this feedback by changing how the device is being operated, or by choosing alternative sanitization goals.

Figure 1A:
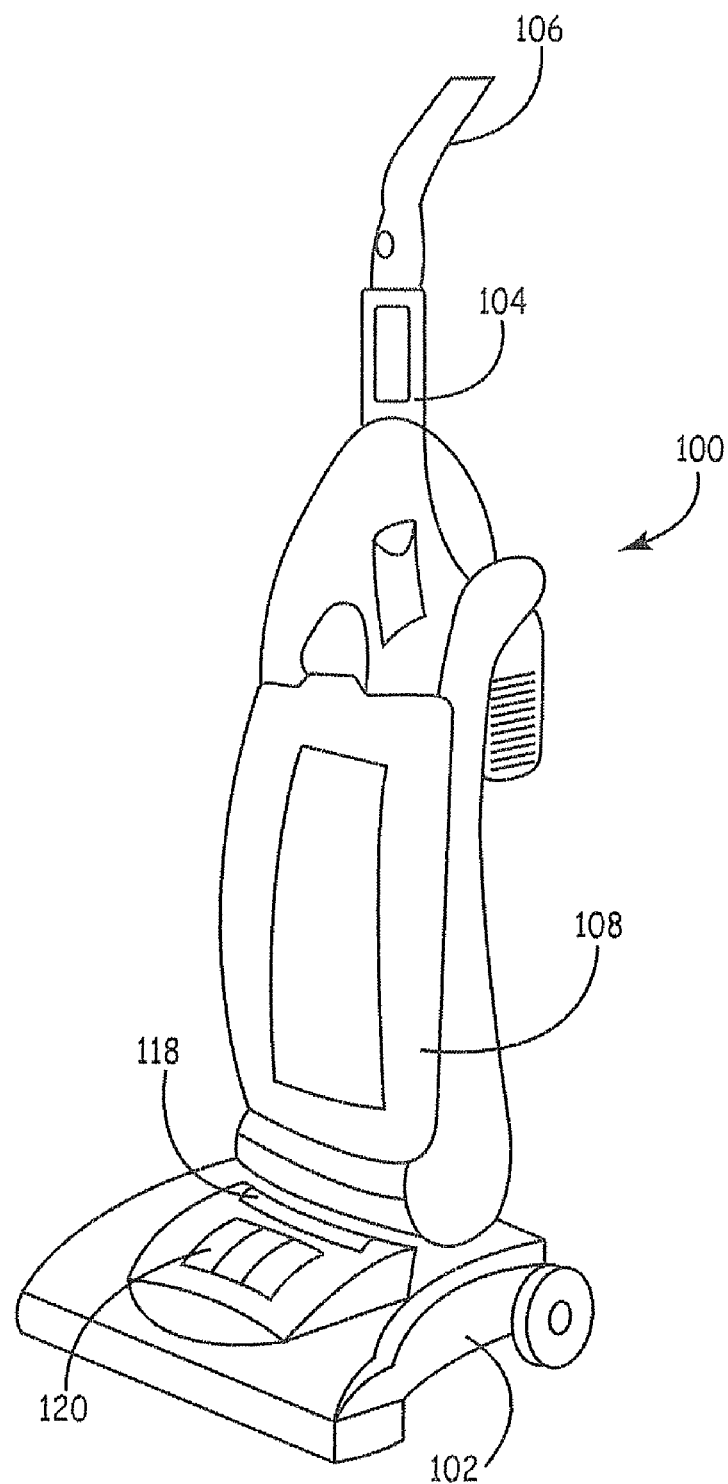
FIG. 1A depicts an upright vacuum with a display for providing information to the user.
Figure 1B:
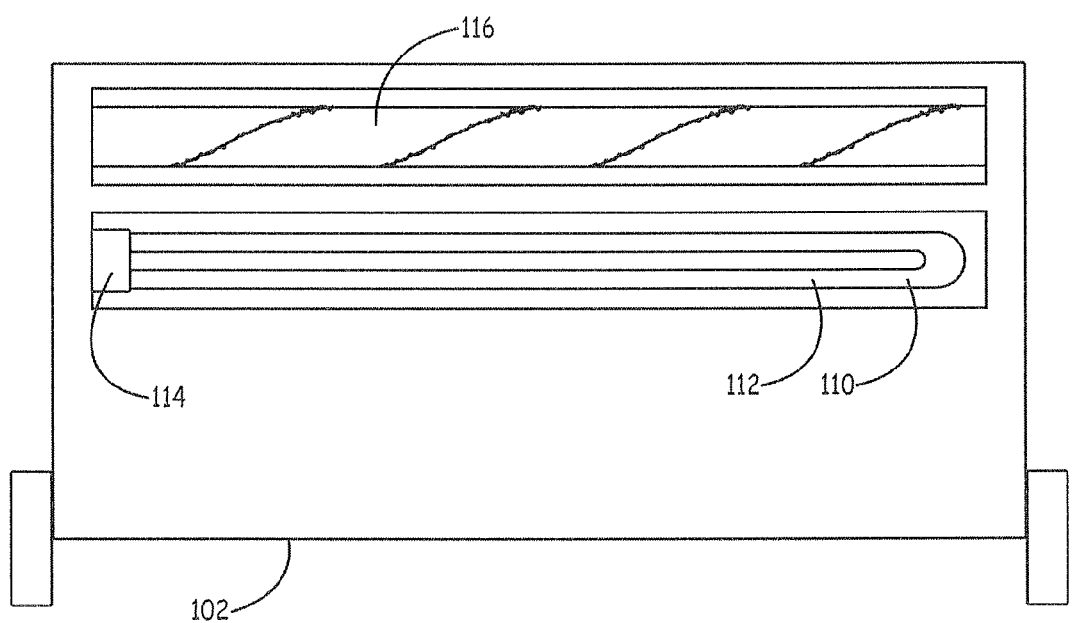
FIG. 1B is a bottom view of the head of the cleaner of the embodiment of FIG. 1A.

FIG. 1 depicts vacuum cleaner 100 having head 102, handle 104, and grip 106. Bag 108 is affixed to handle 104. The vacuum cleaner is equipped with a germicidal light source 110 having bulb 112 and base 114. The light source may be provided with safety detection features to turn off when the head is a predetermined distance from the ground or tilted at an angle relative to the surface it is designed to rest upon. The vacuum is equipped with typical components such as a motor and brush 116, as is known in these arts. Head 102 has user input panel 118 and display 120.

Figure 2A:
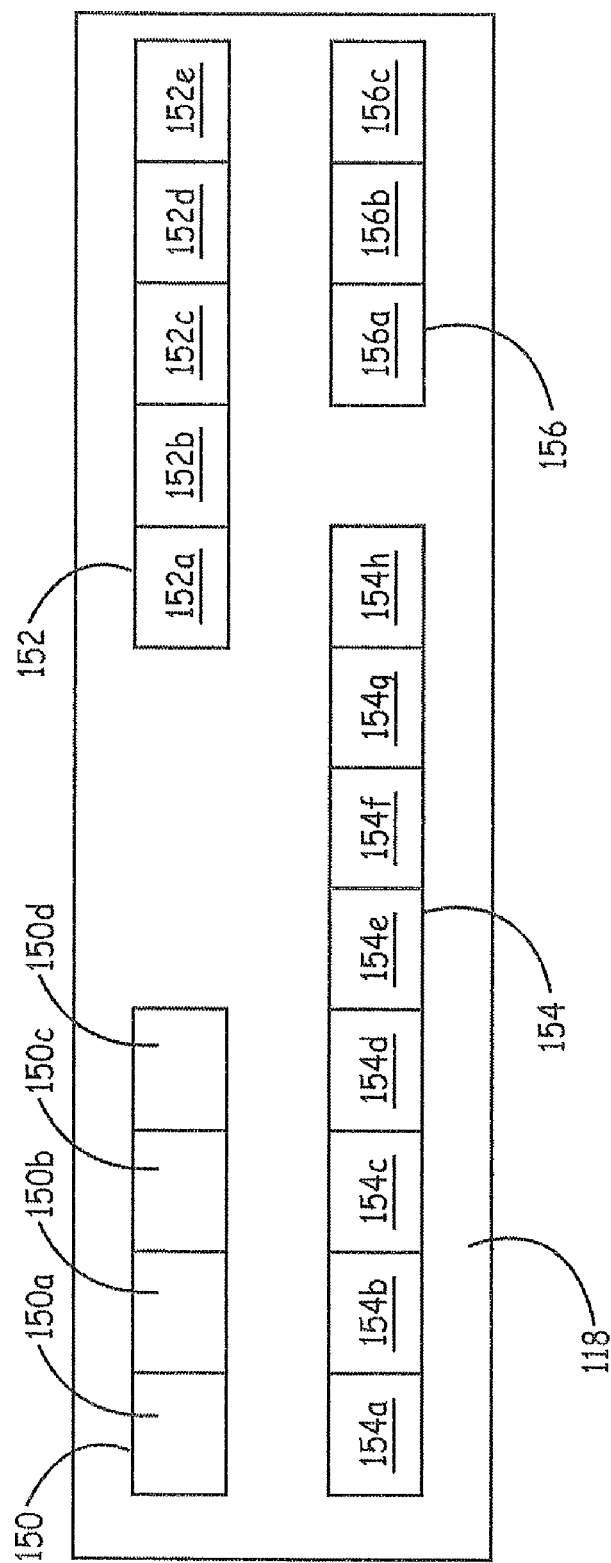
FIG. 2A depicts a display of the embodiment of FIG. 1A.

User input panel 118 depicted in detail in FIG. 2A has a plurality of touch-sensitive buttons for user input. Subpanel 150 has buttons 150a, 150b, 150c, 150d for input of floor types: smooth, carpeted, medium carpet, thick carpet, respectively. User input panel 152 has buttons 152a, 152b, 152c, 152d, 152e for input of the number of passes over the surface are intended, e.g., from 1 to 5, respectively. The number of passes refers to the number of times the light source is to be passed over a targeted surface area. Panel 154 has buttons 154a through 154h, that indicate the predetermined dosage that is to be applied. Panel 156 has buttons 156a, 156b, and 156c for input of surface sensitivity, e.g., delicate, sensitive, or normal.

Figure 2B:
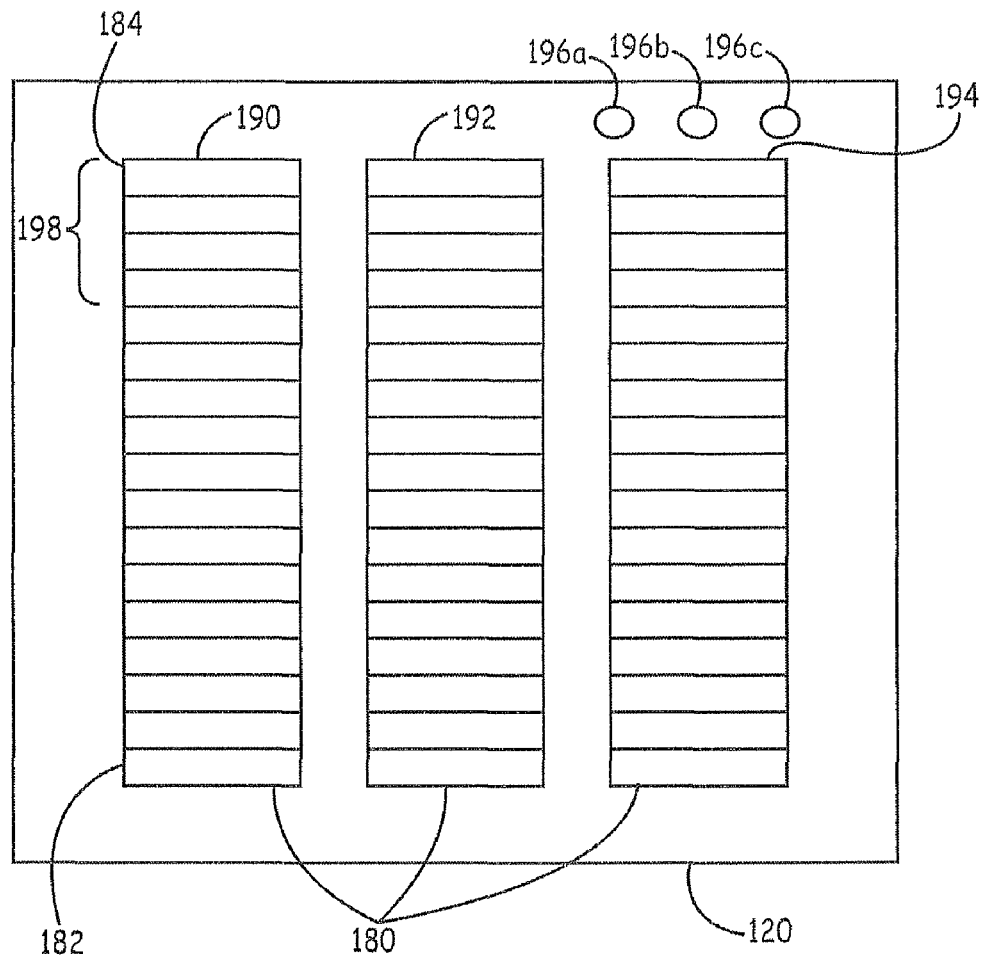
FIG. 2B depicts a display of the embodiment of FIG. 1A.

Display 120 depicted in detail in FIG. 2B has a plurality of light bar strips 180. Lights in the strips 180 are illuminated light from bottom 182 to top 184. Strip 190 indicates to the user an intensity of the source, with illumination of one or a few lights indicating a lower intensity relative to the illumination of a greater number of the lights. Strip 192 indicates a target speed for the user to move head 102 relative to the floor. Strip 194 indicates an actual speed of movement of head 102. Lights 196a, 196b, 196c indicate the quality of a match between actual and desired speed, with light 196a indicating a user speed that is low, light 196b indicating an on-goal speed, and light 196c indicating a speed that is fast. Lights indicated at bracket 198 signify an intensity burst of germicidal light source 110, with the burst being provided only for a limited time.

A user selects a variety of inputs to set initial intensity of source 110. A user selects a floor type from options on sub-panel 150, an intended number of passes from input panel 152, and a predetermined dosage using panel 154. The type of floor can affect the required light dose, with smooth, hard floors requiring the lowest dose and a thick shag carpet requiring a higher dose. A user that intends to make two passes over a target area with the vacuum cleaner may select that option on panel 152, with internal logic and microprocessor algorithms in cleaner 100 accounting for the same. The user simply adapts a coverage pattern for covering the area twice. Alternatively, a user that prefers to cover an area four times would select an option for four passes. The user also selects a dose using panel 154. Each button 154a-154h is labeled with a disease, condition, or organism, with the necessary dosage increasing from 154a to 154g. In the depicted embodiment, the buttons are labeled typhoid, influenza, hepatitis, anthrax, mold A, mold B, dust mite, and bed bug. Further options include, for instance, viruses, bacteria, mold, and pests. Other options are to provide settings labeled on a scale, e.g., a numeric scale of 1-10 or 1-5, or qualitative settings such as high, medium, and low, with instructions being provided with the device to indicate which setting is best suited to the elimination of undesired organisms or conditions.

Alternatively, a dose may be indicated in units (e.g., $J/cm^2$) or numerically, e.g., 1-8. The vacuum cleaner may further be equipped with automatic detectors. These may be configured to detect, e.g., the surface type, distance to the surface, and surface roughness. A user may select buttons from panel 156 to set surface sensitivities; in this embodiment, selection of a delicate or a sensitive surface sets an intensity limit that can not be exceeded, with microprocessor instructions in the vacuum cleaner serving as an electronic governor of the light source intensity.

After providing suitable inputs, a user activates the vacuum cleaner and moves it across the surface to be cleaned. The user-input and/or automatic inputs from the automatic detectors provide an initial intensity. Display 120 provides information to the user to indicate if the user's movement of head 102 is fast or slow. If the user's speed is too fast or too slow over an averaged period of time, the intensity of source 110 is automatically adjusted and strip bar display 190 is accordingly adjusted.

Figure 3:
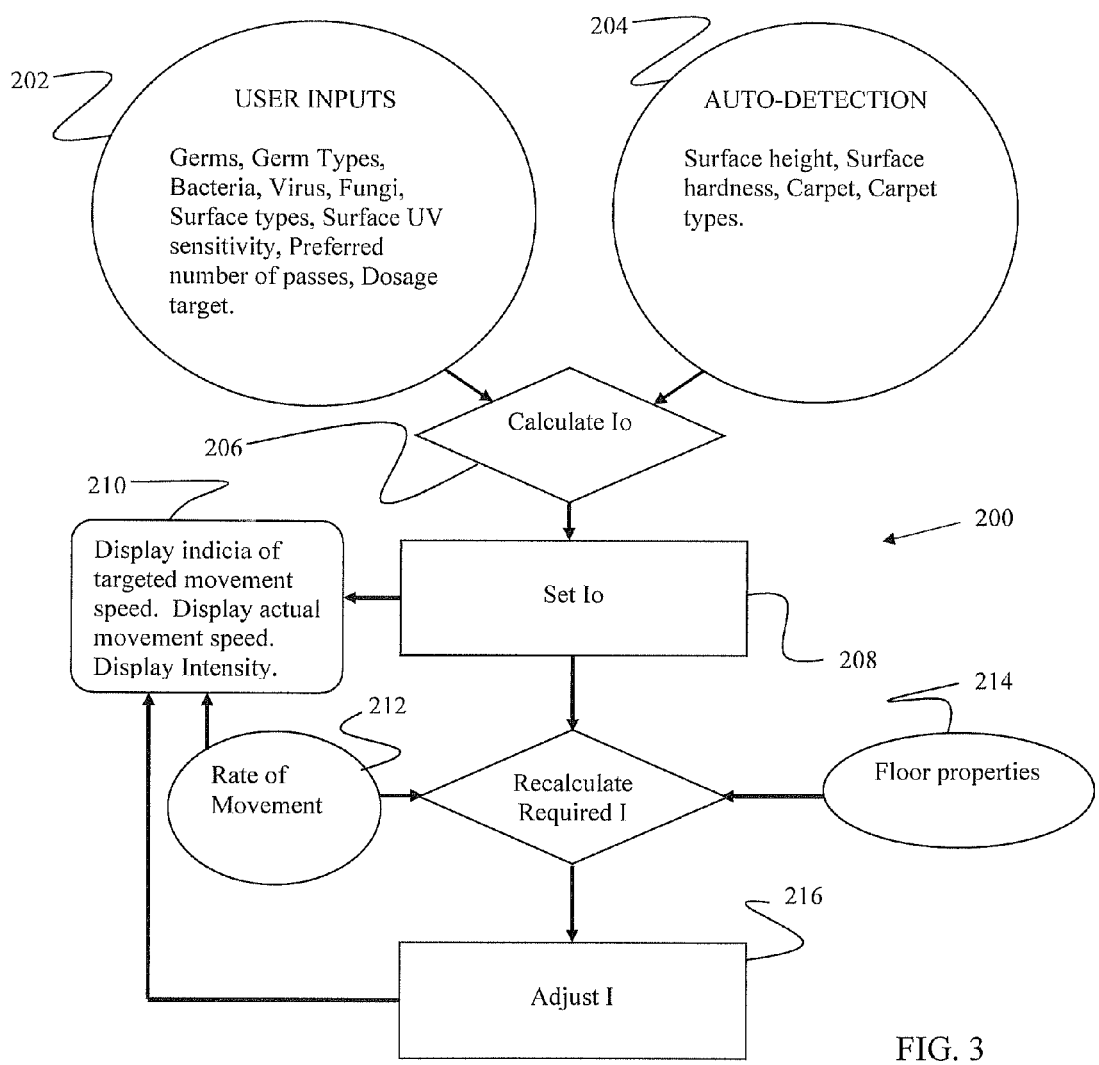
FIG. 3 is a flowchart depicting a control for a mobile sanitizing device.

FIG. 3 depicts flow chart 200 describing interaction of user and automatic conditions. User inputs 202 and automatically-detected inputs 204 are combined, at 206, to calculate an initial intensity setting, Io. The light source 110 is then started at that intensity, as at 208, and displays are activated indicate the target movement speed, as at 210. When the cleaner 100 is in motion, auto-detection 212 and movement detectors 214 provide data to the internal microprocessor to drive the displays and for potential recalculation and adjustment of intensity, as at 216.

The light source may be an ultraviolet light (UV) source, e.g., ultraviolet A (UVA; about 400 nm to about 315 nm) and/or ultraviolet B (UVB; about 315 nm to about 290 inn) and/or ultraviolet C (UVC; about 290 nm to about 100 nm). These are germicidal light sources. UVC sources can be found in mercury arc lamps and light sources commonly referred to as germicidal or UVC lamps. Some light sources are referred to as high pressure UVC lamps, and typically have a peak at about 254 nm and a secondary peak at about 185 nm. Medium pressure UVC lamps vary somewhat and typically have multiple peaks from abort 225 nm to about 600 nm.

A light source may be UV, visible light, or a UVC light source, for instance, having a power rating from about 1 to about 150 Watts; artisans will immediately appreciate that all the ranges and values within the explicitly stated ranges are contemplated, e.g., 1 to about 40 Watts, 60 Watt, or 80 Watts, or from 20 Watts to 80 Watts. In some embodiments, the UVC light source emits a peak at about 254 nm but not at about 185 nm; accordingly, some embodiments are free of light emitted at about 185 nm. Another light source embodiment is a mixture of UVA and/or UVB and/or UVC light in the range of about 185 nm to about 365 mm. The light may come from a filtered broad spectrum light source to provide a spectrum of light within the 185-365 range, or a plurality of light sources may be used that each provide at least one peak within the 185-365 range. Moreover, the light source may exclude wavelengths outside of the 185-365 range.

The intensity at the surface that receives the light is not the same as the intensity at the bulb. The intensity at the surface depends upon a variety of factors including the efficiency of directing light from the bulb to the surface and the distance from the bulb to the surface. An embodiment of the invention is a device equipped with a UVC source that provides at least 20,000 microWatts per square centimeter ($\mu W/cm^2$) UVC light at a surface. The UVC source may be operated with an output of, for example, more than about 20,000 $\mu W/cm^2$; artisans will immediately appreciate that all the ranges and values within the explicitly stated ranges are contemplated e.g., 35,000 $\mu W/cm^2$ or 60,000 $\mu W/cm^2$, or between about 20,000 $\mu W/cm^2$ and 150,000 $\mu W/cm^2$.

The cleaning mechanism of UV light is a photochemical process. Organisms or other compounds undergo breakdown when exposed to high intensity UV at about 240 to 290 mm. Short-wave ultraviolet light can destroy DNA in living microorganisms and breakdown organic material found in indoor air. UVC light's effectiveness is directly related to intensity and exposure time. UV rays strike contaminants directly to penetrate it and break down its molecular bonds. This bond breakage translates into cellular or genetic damage.

For instance, the required UVC light dosage for a 99.9% kill rate of typhoid on a smooth control surface is about 6000 $\mu Ws/cm^2$. The 99.9% kill rate for influenza is achieved at a UVC light dosage of about 6600 $\mu Ws/cm^2$. The UVC light dosage to achieve 99.9% kill rates for hepatitis, anthrax, Mold A, and Mold B are about 8,000, 8700, 10,000, and 44,000 $\mu Ws/cm^2$, respectively. Some embodiments accordingly relate to exposing a target area to a light source to sterilize the area for a particular condition or organism causing the condition until the target area is exposed to at least a dose of light that sterilizes the surface, meaning a 99.9% kill rate as measured under controlled conditions. Other embodiments relate to sanitizing a surface target area, meaning that the area is exposed to a dosage of light calculated to remove unwanted compounds without fully sterilizing the surface, e.g., about 25% to about 99.9%; artisans will immediately appreciate that all the ranges and values within the explicitly stated ranges are contemplated, e.g., from about 50% to about 80%. Certain methods of use include shining a UV light at an object for a predetermined amount of time to achieve the predetermined dose as guided by the output of the source light and its intensity at the target surface.

Embodiments include a germicidal light source mounted on a mobile device. Mobile refers to a device that moves to pass the sterilizing light source over the target area and is in contrast to a static device that sterilizes without direct movement. Accordingly, a device that is left in a room to sterilize the room without being moved is static. A hand-held device that a human user moves during a cycle is mobile, as is a robot equipped to move about an area, a robotic floor vacuum cleaner. A device that receives a component for sterilization into an enclosed chamber is static. The device may comprise a microprocessor and/or sensors and/or displays or other features as set forth herein and by way of incorporation. A vacuum cleaner may be equipped with an ultraviolet light source. The light source may be mounted according to the style of vacuum cleaner to illuminate the surface being vacuumed, e.g., canister or upright, see for example U.S. Pat. No. 2,632,912, U.S. Pat. No. 4,907,316, US 2006-0185116, US 2007-0192986 each of which are hereby incorporated by reference herein to the extent they do not contradict what is explicitly disclosed herein.

The light source may be controlled by a microprocessor, also referred to as a processor herein. In general, a (micro) processor refers to one or more computing devices that compute using hardware, software or firmware. A single microprocessor may be used in many embodiments, or a plurality of microprocessors may share computing tasks. The various processing tasks may be performed by one or more of processors located in one or more of the locations. The term processor is broad and includes devices such as a general purpose computer, a user-programmable chip, and a chip programmable prior to assembly of the device. Accordingly a processor is a term that includes an integrated circuit (also known as IC, microcircuit, microchip, silicon chip, or chip), a miniaturized electronic circuit (semiconductor devices and/or passive components). The processor may encompass a computer-readable medium, e.g., flash storage media, permanent or temporary memory, a registry, random-access memory (RAM), dynamic RAM (DRAM), Z-RAM, TTRAM, A-RAM, volatile memory, non-volatile memory, read-only memory (ROM), magnetic computer storage devices, and optical memory.

The processor may be operably connected to one or more sensors. Examples of sensors are devices that provide data regarding tilt, acceleration, velocity, orientation, speed, temperature, and conditions of a surface. Such sensors include, for example, gyroscopes, accelerometers, tilt indicators, thermistors, infrared sensors, and audio or ultrasound detectors. Gyroscopes include electronic gyroscopes and micro-electro-mechanical system (MEM) gyroscopes, e.g., as made by Systron Donner Inertial. An accelerometer or accelerometers may be used. An xyz accelerometer may be used to provide an object's attitude, i.e., its coordinates in an xyz coordinate system. An xy accelerometer provides acceleration along two axes and other accelerometers provide one acceleration value. An embodiment of a tilt detector is an electronic inclinometer, e.g., of a type in the group accelerometer, liquid capacitive, electrolytic, gas bubble in liquid, pendulum, and MEMS (Micro-Electro-Mechanical Systems).

Other sensors are based on photodetection, with a camera, infrared or other light-based detectors. In general, a distance detect light source (e.g., infrared LED) emits light that is reflected at least partially by a surface; a detector mounted neat the emitter measures the amount of light received, with the emitter typically having a sensitivity matched to the emitted light wavelength. Photodiodes or CCD chips are available as detectors, with triangulation routines being available for enhanced distance calculation. Other detectors based on ultrasound may also be used. Devices may include a wheel for providing distance and/or acceleration and/or velocity and/or speed data. Turning of the wheel indicates traverse according to the direction of the wheel's rotation, with other movement sensors optionally providing data related to, e.g., pivots, turns or circles made by the user.

Some sensors detect temperatures, track time (timers), or current. The current delivered to a light source can be monitored as an indication of intensity at the source, and controlled to adjust the intensity. Temperature at or near the light may be monitored. Timers may be used to measure the time that a light source is on. These data may be integrated and/or compared to determine if and when an intensity of the source is to be adjusted downwardly.

One or more sensors may be used to detect a type or condition of a surface. For example, a distance detector set to a small spot size (focus area) returns information about the roughness of the surface, which may then be processed to distinguish floors from carpets and to indicate a carpet type. An acoustic-based detector returns distinct frequencies in the case of different surface types, and can indicate a hardness and a carpet type and depth. CCD-chip detectors may be used to provide images for sophisticated processor analysis for determination of surface properties. Sensors that detect microbes or microbial types may also be employed. These sensors may be connected to the display and/or the controls. In one embodiment, the sensor changes the light intensity upon detection of a microbe or type of microbe; an example of such a detector is the CLEAN-TRACE NG LUMINOMETER (3M, St. Paul, Minn.). In another embodiment, the sensor provides data used for a display that guides the user to effectively sanitize or sterilize a surface.

A sanitizing device may provide users with options to control settings or choose conditions the user wishes to address. These user-inputs may be provided in many ways, for instance by a button. A button that is actuated by a user is a broad term and may include, for example, a switch, a toggle, a sliding switch that allows adjustable control of the component being switched, hand-actuation, knobs, rheostats, and wheels (e.g., thumbwheel).

For instance, an interactive display or a selection device (e.g., switch, knob, slider) may allow a user to select for one or more sanitization conditions, e.g., mold A, mold B, bed bug infestation, typhoid, influenza, hepatitis, anthrax, mold A, mold B, and dust mite. Further options include, for instance, viruses, bacteria, mold, and pests. Other options relate to the type of surface to be sanitized: hard floors, carpet, deep carpet, deep shag carpet, mattresses, pillows, curtains, drywall, moist, and/or dry. Further options include surface sensitivity, e.g, normal, delicate, fragile.

Another user-input option provides for a user to indicate a number of passes over a target area. Users are accustomed to performing a systematic coverage of an area, e.g., as in vacuuming a room, and may choose the number of passes that they intend to make over an area.

Certain embodiments of the sanitizing devices provide for a display. The term display is broad and includes, e.g., lights, light arrays, liquid crystal displays, and video displays. In general a display may be augmented with, or replaced by, audio signals, depending on the overall functionality of the display. Certain embodiments provide for a microprocessor to receive user and automatic inputs for calculation of an intensity of the light source, and be in operable connection of the source to adjust its intensity, for instance by control of the current provided to the source. The intensity may be adjusted for an increase or for a decrease.

FIG. 3, described in detail above, describes an embodiment that integrates user inputs, automatic detection, and ongoing data collection to calculate, provide, and adjust an intensity. The user inputs and any automatically detected conditions provide for a first intensity setting for a germicidal source. For instance, a microprocessor may be programmed so that selection of mold A provides for a target dose of 10,000 µWs/cm². An input of "smooth" surface and "normal" sensitivity provides for no adjustment upwards or downwards. A selection of "one pass" provides a target movement rate based on the calculated intensity at the surface and the dose; the processor directs a display to indicate a targeted movement rate and turns on the light source.

Movement data, e.g., by accelerometer or wheel, is detected and indicated to a user by an actual speed display. A user may respond by adjusting a rate of movement upwardly or downwardly. If the user's adjustment is not suitable over a predetermined period of time, the microprocessor may direct the light source to be adjusted in intensity and also direct a new displayed target speed. The change in intensity may also be displayed to the user. Other auto-detection features may also be incorporated to adjust the intensity. For instance, a change from an easily sanitized surface to a more challenging one can be detected and the intensity increased. A display may correspondingly be adjusted to communicate the change.

Certain embodiments provide a limitation on intensity. For instance, a "delicate" surface input could limit intensity to a maximum number regardless of other controls. Other embodiments alternatively or additionally include a quick-change function, wherein an intensity of the source is increased or decreased temporarily before returning to a previous value. For instance, a quick movement of the device could trigger a higher burst of intensity, or a slowing or stopping trigger a slow-down. The burst of intensity may be limited to a predetermined amount of time as guided by temperature and source life limitations. For short periods of time the source may be allowed to ramp up to unsustainably high levels (a burst of intensity) to provide immediate coverage for a user moving the device too quickly for the intended sanitization conditions. During the burst process, a display may be used for indicating that a slowing down of the device's speed of movement is required for a sustainable operations.

Displays provided to the user are helpful in guiding the user to effectively sanitize or sterilize a surface. Displays may be used to communicate information to a user, e.g., by one or more lights, numbers, text, graphics, alphanumeric, or an audio signal. The user inputs may be used to define the user's goals and determine intensities based on these or other factors, such as surface conditions. Certain embodiments provide a display of one or more factors chosen from the group consisting of actual movement rate, movement rate goals, and intensity. A display may alternatively or additionally include number of passes, intended dose, condition or organism being targeted for sanitation, sensor output data, or other factors set forth herein. Further, if the intensity or speed is not available to accomplish the user's input goals, an indication of the same may be provided. For example, some settings may require a plurality of passes at a particular speed and/or intensity.

An embodiment is a device with an adjustable intensity or other features as described herein that is also equipped with processing and sensor capabilities to track dosages in a region and display the same. These features are described in U.S. Ser. No. 12/290,113 filed Oct. 27, 2008, which is hereby incorporated herein by reference for all purposes. Accordingly, user settings for initiating a cycle may be used in combination with tracking data to ascertain a dose applied to an area or a subarea. This information may be displayed to a user. Variable source intensities can be accounted for in the dosage accumulation measurements. Moreover, the device may provide an indication or a display showing the user that sanitizing is complete.

An embodiment of the invention is a mobile sanitizer movable across a surface to sanitize the surface comprising a ultraviolet light source that illuminates the surface and a microprocessor control operably controlling the light source intensity to adjust the intensity of the light source as the light source is moved, and in response to a speed of the movement of the light source relative to the surface. For instance, an accelerometer may be used to provide speed data to the microprocessor that is both displayed and also used in calculations for changing an intensity. A user's operation of a device may have considerable variation in speed and direction, e.g., as in a sweeping back-and-forth motion, that is accommodated by averaging a speed over time. The average may be based on absolute values. Similarly, a change in intensity may require a change over a predetermined time interval so as to avoid rapid and frequent intensity changes.

The intensity may be adjusted as needed, e.g., by a factor of between 0.1 and 10, e.g., with a 10% increase being a factor of 1.1; artisans will immediately appreciate that all the ranges and values within the explicitly stated ranges are contemplated. The intensity may be increased or decreased as the device is moving. In contrast, a device that is at rest and shuts off its light source is not adjusting an intensity while it is moving. A processor control may be used to provide a normal maximum intensity and further provides a burst intensity that is greater than the normal maximum intensity, with the burst intensity being limited to a predetermined duration of time.

The device may display to the user that sanitizing is proceeding as planned and/or is complete. In one embodiment, a green light or bar indicates to a user that all of the settings and operation parameters are cooperating to achieve a desired goal, e.g., dosage goal. In general, the device may be provided with instructions that outline usage guidelines, for instance the how long to expose an area to achieve various levels of sanitization for a variety of organisms. In one method, the user is instructed to provide a series of passes over the intended target area. Embodiments include a kit that has a hand held sterilizing device and instructions for using the device as described herein.

Patents and publications referenced herein are hereby incorporated herein by reference for all purposes; in case of conflict, the instant specification controls. Certain embodiments have been described with various features. These features may be mixed and matched on the devices as guided by the need to make operative devices.

The invention claimed is:

1. A mobile sanitizer movable across a surface to sanitize the surface comprising an ultraviolet light source that illuminates the surface and a microprocessor control operably controlling a display that indicates to a user when a sanitization process is being successfully executed; wherein the control provides for an intensity of the light source to decrease in response to a decrease of the speed and also provides for the light intensity to increase in response to an increase of a speed of movement of the light source; or wherein the control changes an intensity of the light source in response to a change in a condition at the surface.

2. The sanitizer of claim 1 wherein the control further provides for an intensity of the light source to decrease in response to an decrease of a speed of movement of the light source.

3. The sanitizer of claim 1 wherein the control further provides for an intensity of the light source to increase in response to an increase of a speed of movement of the light source.

4. The sanitizer of claim 3 comprising a sensor that detects a speed of movement of the light source and provides data on the speed to the controller to adjust an intensity of the light source.

5. The sanitizer of claim 1 wherein the control adjusts an intensity of the light source in response to a speed of movement of the light source to provide a predetermined dose of the light to the surface.

6. The sanitizer of claim 5 wherein the control provides a normal maximum intensity and further provides a burst intensity that is greater than the normal maximum intensity, with the burst intensity being limited to a predetermined duration of time.

7. The sanitizer of claim 1 wherein a user-input control provides an adjustment of an intensity of the light source.

8. The sanitizer of claim 7 wherein the user-input control provides for an input chosen from the group consisting of a hard surface, a carpeted surface, a mattress surface, a fabric, a drape, and an upholstered surface.

9. The sanitizer of claim 7 wherein the user-input control provides for an input chosen from the group consisting of: sanitization for viruses; sanitization for a bacteria; sanitization for a pest; and sanitization for molds and/or fungi.

10. The sanitizer of claim 1 wherein the control limits a maximum intensity of the light source to a predetermined maximum value and provides a non-zero minimum intensity while the sanitizer is moving.

11. The sanitizer of claim 10 further comprising a user control to turn off the light source.

12. The sanitizer of claim 1 wherein the control further increases or decreases an intensity of the light source in response to a change in a condition at the surface.

13. The sanitizer of claim 12 wherein the condition is chosen from the group consisting of hardness and roughness.

14. The sanitizer of claim 12 further comprising a surface detector that detects a condition of the surface.

15. The sanitizer of claim 14 wherein the surface detector is chosen from the group consisting of a photodetector, acoustic detector, capacitance detector, and resistance detector.

16. The sanitizer of claim 14 wherein a condition of the surface is chosen from the group consisting of carpet, deep carpet, hard, smooth, rough, fabric, upholstery, and drape.

17. The sanitizer of claim 1 wherein the ultraviolet light source is an ultraviolet C light source.

18. The sanitizer of claim 1 wherein the display indicates a target speed and the speed of movement.

19. The sanitizer of claim 18 wherein the display indicates an intensity of the light source.

20. The sanitizer of claim 1 wherein the display indicates when the light source is providing a burst of increased intensity.

21. A process of making a mobile sanitizer for sanitization of a surface by an ultraviolet light source comprising preparing a microprocessor control to
   (i) adjust the intensity of the light source as the light source is moved and in response to a speed of the movement of the light source relative to the surface and/or
   (ii) control a display to indicate to a user a indicating a target speed and a speed of movement of the light source relative to the surface.

22. The process of claim 21 wherein the sterilizer further comprises a display indicating when a sanitization process is being successfully executed.

23. The process of claim 21 wherein the control provides for the light intensity to decrease in response to a decrease of the speed and also provides for the light intensity to increase in response to an increase of the speed.

24. A method of sanitizing a surface with a mobile sanitizer that directs light from an ultraviolet light source onto the surface, the method comprising:
   selecting a plurality of settings to achieve a light dosage goal, moving the sanitization device across the surface; wherein the sanitizer automatically adjusts an intensity of the light source in response to a speed of the movement of the light source relative to the surface; or wherein the sanitizer further increases or decreases an intensity of the light source in response to a change in a condition at the surface.

25. The method of claim 24 further comprising adjusting a speed of the movement in response to a display indicating that the speed requires an adjustment to meet the goal.

26. The method of claim 24 wherein the device automatically adjusts an intensity of the light source in response to a speed of the movement of the light source relative to the surface.

27. A mobile sanitizer movable across a surface to sanitize the surface comprising an ultraviolet light source that illuminates the surface and a microprocessor control operably controlling a display that indicates to a user when a sanitization process is being successfully executed; wherein the control automatically adjusts an intensity of the light source in response to a speed of the movement of the light source relative to the surface; or wherein the control changes an intensity of the light source in response to a change in a condition at the surface.

28. A mobile sanitizer movable across a surface to sanitize the surface comprising an ultraviolet light source that illuminates the surface and a microprocessor control operably controlling the light source intensity to adjust the intensity of the light source as the light source is moved and in response to a speed of the movement of the light source relative to the surface.

* * * * *